US010980456B2

(12) United States Patent
Gupta

(10) Patent No.: US 10,980,456 B2
(45) Date of Patent: Apr. 20, 2021

(54) METHOD AND APPARATUS FOR LIGHT-WEIGHT, NON-INVASIVE, POINT OF CARE DIABETES SCREENING DEVICE

(71) Applicant: Rijul Gupta, San Francisco, CA (US)

(72) Inventor: Rijul Gupta, San Francisco, CA (US)

( * ) Notice: Subject to any disclaimer, the term of this patent is extended or adjusted under 35 U.S.C. 154(b) by 0 days.

(21) Appl. No.: 16/312,080

(22) PCT Filed: May 22, 2018

(86) PCT No.: PCT/US2018/033911
§ 371 (c)(1),
(2) Date: Dec. 20, 2018

(87) PCT Pub. No.: WO2018/217765
PCT Pub. Date: Nov. 29, 2018

(65) Prior Publication Data
US 2019/0200904 A1    Jul. 4, 2019

Related U.S. Application Data

(60) Provisional application No. 62/509,325, filed on May 22, 2017.

(51) Int. Cl.
*A61B 5/1455* (2006.01)
*A61B 5/145* (2006.01)
(Continued)

(52) U.S. Cl.
CPC .......... *A61B 5/1455* (2013.01); *A61B 5/0059* (2013.01); *A61B 5/0075* (2013.01);
(Continued)

(58) Field of Classification Search
None
See application file for complete search history.

(56) References Cited

U.S. PATENT DOCUMENTS 3,638,640 A     2/1972  Shaw
8,055,321 B2 *  11/2011 Bernreuter ......... A61B 5/14553
                                                  600/323
(Continued)

OTHER PUBLICATIONS

International Search Report and Written Opinion for PCT/US18/33911, dated Aug. 10, 2018.

*Primary Examiner* — Marjan Fardanesh
(74) *Attorney, Agent, or Firm* — Hahn Loeser & Parks LLP

(57) ABSTRACT

A multi-channel measurement device for measuring properties of human tissue, may comprise a microcontroller and first and second source/sensor complexes. The first source/sensor complex may include a first housing having a first measurement portion, a first light sensor coupled to the microcontroller and exposed to the first measurement portion, and a first plurality of light sources coupled to the microcontroller and exposed to the first measurement portion. The second source/sensor complex may include a second housing having a second measurement portion, a second light sensor coupled to the microcontroller and exposed to the second measurement portion, and a second plurality of light sources coupled to the microcontroller and exposed to the second measurement portion. The first and second source/sensor complexes are coupled to each other such that the first measurement portion is opposite the second measurement portion and human tissue may be placed between the the first and second measurement portions. The microprocessor is configured with instructions stored in non-volatile memory to individually activate each of the light sources of the first and second pluralities of light sources and to record light intensity detected by the first and second light sources while an individual light source is activated. Each combination of an individually activated light source and one of the first and second light sensors (Continued)

provides a distinct measurement channel for measuring the absorption spectra of human blood and tissue.

18 Claims, 10 Drawing Sheets

(51) Int. Cl.
| | |
|---|---|
| *G01J 3/00* | (2006.01) |
| *A61B 5/00* | (2006.01) |
| *G01N 21/31* | (2006.01) |
| *G01N 21/47* | (2006.01) |
| *G01J 3/28* | (2006.01) |
| *G01N 21/49* | (2006.01) |
| *G01J 3/02* | (2006.01) |
| *G01J 3/10* | (2006.01) |
| *G01J 3/427* | (2006.01) |
| *G01J 3/457* | (2006.01) |

(52) U.S. Cl.
CPC ...... *A61B 5/14532* (2013.01); *A61B 5/14546* (2013.01); *A61B 5/6826* (2013.01); *A61B 5/7267* (2013.01); *A61B 5/7475* (2013.01); *G01J 3/00* (2013.01); *G01J 3/0262* (2013.01); *G01J 3/10* (2013.01); *G01J 3/28* (2013.01); *G01J 3/427* (2013.01); *G01J 3/457* (2013.01); *G01N 21/31* (2013.01); *G01N 21/474* (2013.01); *G01N 21/49* (2013.01); *G01J 2003/102* (2013.01); *G01N 2021/3155* (2013.01); *G01N 2021/3181* (2013.01)

(56) References Cited

U.S. PATENT DOCUMENTS

| | | |
|---|---|---|
| 8,418,499 B2 | 4/2013 | Al-Ali et al. |
| 9,597,021 B1 | 3/2017 | Gupta et al. |
| 2003/0109772 A1* | 6/2003 | Mills ................. A61B 5/02028 600/310 |
| 2006/0270920 A1 | 11/2006 | Al-Ali et al. |

* cited by examiner

METHOD AND APPARATUS FOR LIGHT-WEIGHT, NON-INVASIVE, POINT OF CARE DIABETES SCREENING DEVICE

CROSS-REFERENCE TO RELATED APPLICATIONS

This application claims priority to, and the benefit of, International Patent Application No. PCT/US2018/033911, filed May 22, 2018 with the U.S. Patent Office (acting as the US Receiving Office), which claims priority of U.S. Provisional Patent Application No. 62/509,325, filed May 22, 2017, and which is herein incorporated by reference.

FIELD OF THE INVENTION

The field of the invention is non-invasive diagnostic screening devices. In particular, the field of the invention relates to a non-invasive, lightweight diabetes screening device.

BACKGROUND

Diabetes mellitus is a metabolic condition that is characterized by high levels of glucose in the blood. This may be caused by reduced insulin production (as in Type 1 diabetes) or tissue resistance to insulin built up over time (as in Type 2 diabetes). Patients with diabetes suffer increased risks of fatality due from many different causes and generally experience a poor quality of life.

Diabetes can be combated by regular blood sugar monitoring and can even be prevented by early detection. However, more than 8 million people in the US have undiagnosed diabetes, leading to unrestricted development of the disease. Untreated diabetes has negative effects on almost every system in the body. The societal expense of undiagnosed diabetes is $33 billion annually with over $20 billion being paid by government health insurances. Early screening of diabetes and management of the symptoms has been shown to drastically improve patient outcomes compared to similar treatment years later. The potential cost savings on the order of billions of dollars and improvement to life expectancy and quality of life calls for inexpensive, wide scale screening of large populations for diabetes.

Unfortunately, the current diagnostic methods cost at least $15 per person and take 5 minutes per test. The most common FDA approved diagnostic tool is a home immunoassay kit. Each test contains four separate, biologically sterile and accurate parts, three of which are disposed of after use. The high manufacturing costs of these items combined with their lack of reusability contribute the cost of each test, making it prohibitively high for widespread screening.

Known non-invasive technologies cannot be readily adapted to screening for diabetes. For example, pulse oximetry is a known technology for noninvasively measuring blood oxygen levels. Pulse oximetry measures the ratio of oxygenated hemoglobin to deoxygenated hemoglobin in a patient's blood. From this ratio, the oxygen saturation content of a person's blood can be calculated with a reliable degree of certainty. Pulse oximetry makes use of a phenomenon described by the Beer-Lambert law. The Beer-Lambert law relates the passage of light at a constant intensity through a homogeneous substance to the path length the light travels, the concentration of the substance, and the molar absorptivity constant (a measurable property of the substance at a given wavelength). Additionally, the law states that the absorbance of a non-homogeneous substance is the sum of the absorbance of the component homogeneous substances. The Beer-Lambert law allows for an effective approximation for HbO2 at concentrations above 75%.

However, pulse oximetry, and the application of the Beer-Lambert law, is based on the principle that large structural changes exist between oxygenated and deoxygenated hemoglobin, and these have a known change in the absorption spectra. Because these two absorption spectra have an isosbestic point (e.g. they cross), one may use the absorption values of two wavelengths on either side of the isosbestic point to estimate the ratio of oxygenated hemoglobin to deoxygenated hemoglobin at HbO2 concentrations above 75%.

No such known absorption spectra map exists for blood component markers for diabetes. One may assume conformational changes occur which lead to changes in absorption spectra. But these conformational changes may "side-structural" (affecting an isolated portion section of amino acids on the Hemoglobin molecule), occur in small quantities, overlap with other variants (side-structural changes may exist on both oxygenated hemoglobin and deoxygenated hemoglobin for example), may have only small effects on natural properties (like small changes in absorption spectra), may only have local effects on natural properties (like a change in absorption spectra in a narrow wavelength range), and may be non-linear (e.g. they have complex changes in concentration as a function of blood glucose). Therefore, the Beers-Lambert Equation used for pulse oximetry is not useful to diagnose diabetes.

What is needed is a non-invasive device to perform screening of large groups of people over time in a reusable, low cost-per-use manner to screen for medical conditions, such as high levels of glycated hemoglobin. The results of such a low cost screening device may be used to make recommendations for individuals testing positive to receive traditional, higher cost diagnostic testing.

SUMMARY

A non-invasive, reusable device measures light transmission and reflection characteristics through human issue and, with a supervised learning algorithm eliminates the need to know the absorption spectra map (or other natural properties) of relevant blood protein markers a-priori, to screen for medical conditions, such as high levels of glycated hemoglobin. This same technology can be repurposed to a non-invasive, constant blood sugar monitor. By training the learning algorithm on any other clinical property which has effects on the concentration of or natural properties of blood components, we can repurpose the same two technologies for different biological conditions. For example, the device may be trained on measured collagen concentration which is related to blood collagen concentration, fibrinogen concentration, etc, and is clinically associated with heart attacks.

In one example, a multi-channel measurement device for measuring properties of human tissue, may comprise a microcontroller and first and second source/sensor complexes. The first source/sensor complex may include a first housing having a first measurement portion, a first light sensor coupled to the microcontroller and exposed to the first measurement portion, and a first plurality of light sources coupled to the microcontroller and exposed to the first measurement portion. The second source/sensor complex may include a second housing having a second measurement portion, a second light sensor coupled to the microcontroller and exposed to the second measurement portion, and a second plurality of light sources coupled to the microcontroller and exposed to the second measurement portion. The first and second source/sensor complexes are coupled to each other such that the first measurement portion is opposite the second measurement portion and human tissue may be placed between the first and second measurement portions. The first plurality of light sources are angled such that a portion of the emitted light energy is reflected to the first light sensor and a portion of the emitted light energy is transmitted to the second light sensor by human tissue placed between the first and second measurement portions. The second plurality of light sources are angled such that a portion of the emitted light energy is reflected to the second light sensor and a portion of the emitted light energy is transmitted to the first light sensor by human tissue placed between the first and second measurement portions. The microprocessor is configured with instructions stored in non-volatile memory to individually activate each of the light sources of the first and second pluralities of light sources and to record light intensity detected by the first and second light sources while an individual light source is activated. Each combination of an individually activated light source and one of the first and second light sensors provides a distinct measurement channel for measuring the absorption spectra of human blood and tissue.

The first plurality of light sources may produce light at a plurality of different wavelengths. The second plurality of light sources may produce light at a plurality of different wavelengths. For example, the first plurality of light sources may comprise at least five LED light sources configured to emit light at wavelengths different from each other; and the second plurality of light sources may also comprise at least five LED light sources configured to emit light at wavelengths different from each other (although each LED in one plurality of light sources may have a corresponding LED with the same wavelength of light in the other plurality of light sources). In one example, the first plurality of light sources comprises eight LED light sources configured to emit light at wavelengths different from each other; and the second plurality of light sources comprises eight LED light sources configured to emit light at wavelengths different from each other.

The first measurement portion may comprise a first finger cavity and the second measurement portion comprises a second finger cavity.

The microprocessor may be configured with instructions stored in non-volatile memory to provide signals to adjust a light intensity emitted by an individually activated light source based on a light intensity detected by the first and second light sources. The first and second light sensors may comprise light to frequency converters. The first and second light sensors may be recessed in their respective housings to reduce detection of interfering light. The multi-channel measurement device may further comprise a light barrier around each of the first and second light sensors to reduce detection of ambient light.

The multi-channel measurement may further comprise an additional light source and light sensor combination for use as an external reference point.

The multi-channel measurement device may further comprise a processor coupled to the microcontroller and configured with instructions stored in non-volatile memory which, when executed, cause the processor to: signal the microcontroller to begin a measurement cycle; receive measurement data obtained by the microcontroller; and process the measurement data to obtain a clinical result.

The multi-channel measurement device may further comprise a trained neural network, wherein processing the measurement data to obtain a clinical result comprises inputting the measurement data to the neural network.

In another example, a system for measuring properties of human tissue and returning a clinical result, may comprise a neural network, a multi-channel measurement device, and a user interface. The neural network may be trained on a known data set having multiple measurement channel data corresponding to an absorption spectra of human blood and tissue to identify a clinical result from the data. The multi-channel measurement device may be as described in the above example, and further comprising a communications interface. The multi-channel measurement device further being configured to transmit measurement data to the neural network. The user interface may be configured to receive a clinical result identified by the neural network and display it to a user. The user interface may be located on the multi-channel measurement device.

The neural network may be located on a server remote from the multi-channel measurement device. The neural network may be located on a server remote from the multi-channel measurement device and the user interface is on a mobile device. The neural network and the user interface may be located on a mobile device.

BRIEF DESCRIPTION OF THE DRAWINGS

FIG. 3b is another view of a combination of LED complexes of FIG. 3a.

FIG. 3c is another view of a combination of LED complexes of FIG. 3a.

DETAILED DESCRIPTION

Figure 1:
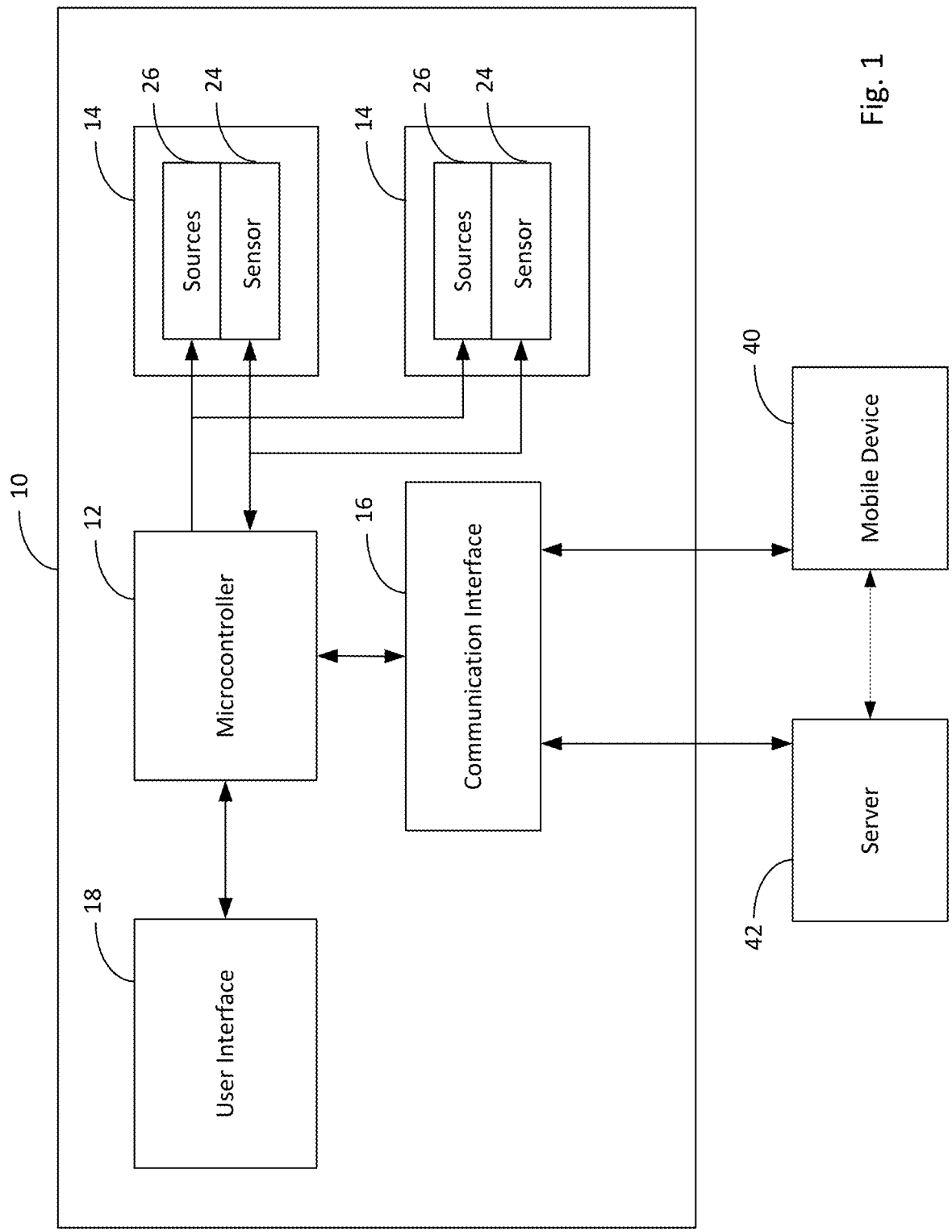
FIG. 1 is a block diagram of a multi-channel measurement device according to one aspect of the present invention.

Blood is comprised of many components. Each blood component has a specific biomolecular structure which has an effect on natural properties like absorption spectra, electrochemical response, etc. The contribution of each blood components natural property on the overall natural property of a given blood sample is a function only of that components natural property and that blood components concentration.

One of the most abundant blood components is the protein hemoglobin (Hb), often attached to red-blood-cells. Hb has many different variants, with variant HbA comprising ~95%. Variations in Hb cause structural changes which are accompanied by changes in the absorption spectra. Some of these changes are large, like the binding of oxygen to a heme group, and can be measured non-invasively easily. Other forms of hemoglobin include those created by the gradual binding of glucose and are accompanied with subtle, often nonlinear structural and spectral changes.

"Glycated hemoglobin" as used herein, means any form of red-blood-cell hemoglobin in which a glucose molecule has been attached to one or more amino acid residues. It is not known how many residues glucose can bind to, but there are at least 23. See, for example, Effect of obesity and glycated hemoglobin on oxygen saturation in ambulatory type 2 diabetic individuals: A pilot study, Diabetes & Metabolic Syndrome: Clinical Research & Reviews Volume 10, Issue 3, July-September 2016, Pages 157-160. A "glycated variant" as used herein means a reversible and/or irreversible form of glycated hemoglobin with distinct conformational properties and therefore distinct natural properties like absorption spectra, electrochemical response, etc. Irreversible glycated variants are formed over time at a rate which is a function of current blood glucose and decay as red blood cells decay or sooner. Reversible glycated variants are formed by the instantaneous binding or nonbinding of glucose; their concentration is a function of blood glucose concentration, and is often non-linear and complicated. A variant may be both reversible and irreversible as a reversible change may be possible after an irreversible change has occurred—thus the variants concentration profiles will have both the reversible and irreversible aspects described above.

HbA1C as used herein refers to one or more reversible/irreversible glycated variants formed by the irreversible binding of glucose to either or both of the B-chain N valine terminal and is a commonly used diabetic marker. The binding to either/both B-chain N valines may be present in one or more glycated variant, but all such variants are measured as HbA1C. Elevated levels of blood glucose increase the exposure of hemoglobin to glucose, which increases the overall glycation of hemoglobin, and leads to a greater formation of HbA1C over time. HbA1C is degraded as the end of a red blood cell's life cycle (usually about three months). With this in mind, the concentration of HbA1C can often be determined as a function of blood glucose over time (similar in shape to most/all irreversible glycated variants). For this reason, measurement of HbA1C is used as a metric for long term blood glucose control for known diabetics. Measurement of HbA1C is also FDA approved as a screening tool for diagnosing diabetes and prediabetes.

The normal HbA1C range for healthy adults is between 4.0% and 5.6%. Ranges below this value indicate hypoglycemia and generally low blood glucose. A measured HbA1C in the range of 5.7% to 6.4% indicates prediabetes, a condition marked by slightly elevated blood glucose levels but missing the insulin intolerance hallmark of diabetes. At this stage, the disease can be cured. A measured HbA1C above 6.5% indicates diabetes and elevated blood glucose. Patients with diabetes may have HbA1C lower than 6.5% if they control their blood sugar well. Generally, patients with undiagnosed diabetes will HbA1C values much higher than 6.5% due to poor blood sugar control.

Differences in long-term blood sugar levels will have a distinct and predictable effect on the concentration of all irreversible glycated variants. In so much as these long-term blood sugar levels indicate the average resting blood glucose at any given time (normal: 120-200 Mg/DL|pre-diabetic: 150-230 Mg/DL|diabetic: above 200 Mg/DL), a distinct effect on the concentration of all reversible glycated variants may be expected. Differences in short-term blood sugar level will have a very small, distinct, and predictable effect on the concentration of all irreversible glycated variants, but may cause large differences on the concentration of reversible glycated variants. These effects may often be binary where one variant is formed in large quantities as a certain glucose threshold is hit and/or then may decrease in large quantities as a different glucose threshold is hit.

Because these changes in long-term and short term blood sugar levels have an effect on the concentration of glycated variants (and possibly other blood components), they have an effect on the contribution of each of these components natural properties to the natural properties (e.g. absorption spectra, electrochemical response, etc) of a person's blood. These effects, however, are often not immediately apparent due to small component concentrations, the similarity of absorption spectra of variants in at certain wavelengths, non-linear/complicated conformational changes, etc. Given these problems, a useful, predictive relationship between the information contained in captured sensor data and long-term or short-term blood sugar cannot be discerned using regular or advanced pulse oximetry.

A multi-channel measurement device is provided herein to measure one or more specific natural properties of a person's blood with a high enough accuracy, precision, resolution, and sensitivity to non-invasively measure these long-term and short-term blood sugar effects on the relative concentrations of each blood component. "Multi-channel", in this context, means multiple combinations of signal sources and measurement sensors, and/or multiple measurements taken under different conditions. For example, measurements may be taken by one light sensor receiving light from several light sources at different angles, providing both transmissive and reflective measurements. Additionally, multispectral measurements may be made, providing additional measurement channels at different wavelengths of light. For example, at least five bands of wavelengths, and preferably at least eight bands of wavelengths of visible, near infrared, or ultraviolet light, and combinations thereof, may advantageously be used to implement the invention. Also, while the specific examples given herein measure light absorption during transmission through human tissue with blood, or reflected from such tissue, the invention is not so limited. Additional sensors, such as electrogalvanic sensors, may also be included to obtain additional measurement channels.

Referring to FIG. 1, a multi-channel measurement device 10 according to one example of the present invention comprises a microcontroller 12 and at least one Source/Sensor complex 14. In a preferred embodiment, at least two Source/Sensor complexes 14 are provided. The microcontroller 12 may include microcode stored in firmware or other non-volatile memory. The microcontroller communicates with and controls operation of Sources 26 and Sensors 24 of the Source/Sensor complexes 14. The Source/Sensor complexes record one or more specific natural properties non-invasively with a focus on accuracy, precision, resolution, and sensitivity. A communications circuit 16 may be included for interfacing with diagnostic tool or application on another device, such as a mobile telephone 40 or server 42, may also be provided.

The microcontroller 12 operates in combination with a "master" Control Program. The master Control Program may be stored on the multi-channel measurement device 10, the mobile device 40, or server 42, or a combination thereof. The Control Program processes and interprets signal information received from sensors 24. The multi-channel measurement device 10 may also include a user interface 18. The user interface 18 may comprise control buttons, status LEDS, a display, a touch sensitive display, or any combination thereof.

In operation, the sensors 24 deliver data to the microcontroller 12. If the signal is a square wave with a variable frequency (as in a TSL237 light to frequency sensor), the microcontroller may conduct some initial processing to transform the square wave into an "intensity" value. The microcontroller may make an initial interpretation and action to control either the sources 26 or sensors 24. It can simultaneously pass this information to the Control Program along with other information about the state of the system.

The microcontroller may increase the source strength to a max threshold, then reduce it to an optimum band. If the signal is too weak, the Control Program may increase the resolution of the microcontroller by "overclocking" or "bit-shifting", thereby increasing the strength up to 8 times. The microcontroller may be configured to pass all sensor data to the Control Program as it comes in. The Control Program may save the data, send the data to a server, or both. The microcontroller may further be configured to provide information about the state of the system (e.g. each sensor resolution, which source is activated, strength of the source) and a unique user identifier to the Control Program.

The microcontroller may adjust the sensor resolution or shut off the sensor if the source signal strength is too intense. The microcontroller may also signal the sensor to increase or decrease resolution. The microcontroller may also signal one or more sources 26 to change source strength or turn this source off and move to another source Microcontroller 12 records sensor readings determines the state of each source in a predefined manner or "on-the-fly" using a web api. Once data capture is complete, the information is normalized and interpreted through an on-device neural network or sent to the web api which returns the interpretation. The device then responds to the patient using an on-device screen or through a connection to a mobile phone.

Figure 2:
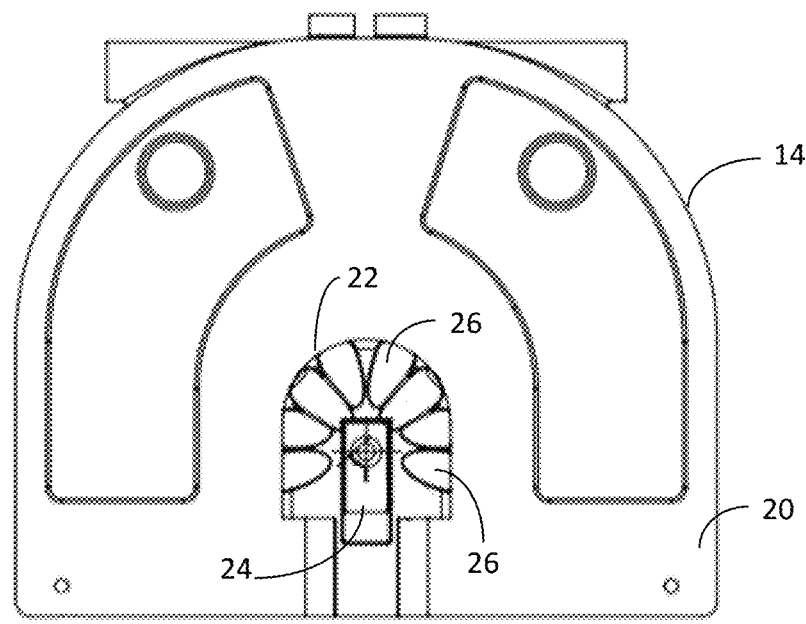
FIG. 2 is an illustration of an LED complex for use in a multi-channel measurement device according to another aspect of the present invention.

One example of a Source/Sensor complex 14 is illustrated in FIG. 2. A Source/Sensor complex typically comprises at least one sensor which monitors a natural property of interest and at least one source which outputs energy of the type monitored by the sensor. In the example of FIG. 2, Source/Sensor complex 14 comprises a housing 20, a finger cavity 22, a sensor 24, and a plurality of sources 26. The sensor 24 is located in the finger cavity 22 such that the housing 20 provides shielding to exclude ambient optical radiation (or other interference) from the tissue to be measured. The sources 26 are positioned relative to the sensor 24 such that enough output signal from the sources 26 is delivered through the tissue to be measured by the sensor 24. Each source 26 may have one or more properties that distinct from the others sources 26 in a way relevant to the natural property being measured. The sources 26 may be arranged to surround the sensor 24 with a one or more known geometries that can be used to extract data which embodies relationships to a diagnosable medical condition. The magnitude of the output of each source 26 may be increased or decreased. The sensor 24 records data over time so that, for example, blood component analysis can be interpreted from a single source if a pulse waveform is detectable.

In the example illustrated in FIG. 2, the sensor 24 may comprise a high sensitivity light-to-frequency converter decoupled with a 0.1 µF capacitor to measure the absorption spectra of a blood sample. One example of such a sensor is a TSL237. The sensor 24 may be slightly recessed in the finger cavity 22 to reduce the potential for ambient light from interfering with the sensor 24. The sensor 24 may record data over time to detect a pulse waveform. Also, in addition to the finger cavity 22, the measurement portion of the device may vary in size and shape depending on the body part and/or tissue to be measured.

The sources 26 may comprise high power LED sources. The sources 26 should have high enough power output, specific orientation angles, and be positioned sufficiently close to the skin to enable sufficient light to reach the sensor 24 to enable reliable measurements. Modifications to LED housings/lenses may be necessary to provide sufficient transmission of radiated energy from the LED to the skin/tissue being measured. Each LED source may comprise a plurality of LEDs of different wavelengths in a single package, or multiple LEDs in separate packages grouped together. For example, LED sources having diodes for red, blue and green wavelengths of light may be used advantageously in the present invention.

The LED sources preferably have narrow illumination beams and narrow wavelength spectrum to increase accuracy and precision. To provide distinct measurement bands, each LED may have or be configured with a wavelength band that is distinct from others. Typical center wavelengths may range from 330 nm to 880 nm. The width of each wavelength band, and the spacing of the center wavelengths, may be selected to cover the visible light spectrum and into the infrared or ultraviolet spectrum. The LEDs surround the sensor in a way that enabled extraction of information about tissue size and/or shape. The LED brightness can be increased/decreased.

In use, the LED sources 26 are individually activated by the microcontroller 12 and the light energy they produce is directed onto the surface of a patient's skin. The light is partially absorbed and partially transmitted through or reflected by (depending on measurement geometry) the patient's tissue and blood. The light sensor 24 detects the intensity of transmitted or reflected light, and provides a signal back to the controller indicative of light intensity. Each of the source/sensor combinations may be considered a different measurement channel.

Other examples of sources/sensors include a Voltage/Galvanometer complex where distinct sources have different impedances or the impedance of each source can be changed and the voltage of each source can be increased/decreased. Each source can also serve as a sensor and vice-versa. Such combinations may also be considered measurement channels. The voltage sources surround the galvanometer in a way that enabled extraction of information about tissue size and/or shape. Optical and electrical sources and sensors may be combined in the same measurement device and used concurrently.

The sources 26 and sensor(s) 24 in the Source/Sensor complex are connected to a microcontroller which operates the sources and monitors all sensor readings. The microcontroller may be configured to operate each source 26 independently of each other, and to adjust intensity and/or wavelength band. This may be done using a predefined schedule, a computer/mobile app interface, or a web api. The microcontroller may shut off sensors that are overloaded by sources which must operate at high magnitudes to interact with other sensors in the system. The microcontroller may be configured to interpret the final sensor data or send this data to a web api which interprets the data and returns a result. The result can be communicated to the user with an on-device screen, or through the use of a mobile app. The microcontroller can be adapted to improve resolution.

In Source/Sensor complexes 14 having multi-band LED sources (e.g., RGB LEDs), the LEDs may be connected to the microcontroller through a plurality of resistors of different values. All sources 26 are connected to the microcontroller by short leads. The microcontroller can change which LED is illuminated and change the brightness emitted by an LED by driving current through different resistors. The controller can specify the LED and strength through a computer program, a predefined schedule, a mobile app, or a web api. The microcontroller can shut off LEDs which overload any sensor, or shut off the sensor which is overloading. The final sensor data can be interpreted by the microcontroller or sent to a web api for interpretation and returning of the result. The final result can be communicated to the user with an on-device screen or through the use of a mobile app. The microcontroller may be "bit-shifted" to allow for an 8× increase in resolution.

Figure 3A:
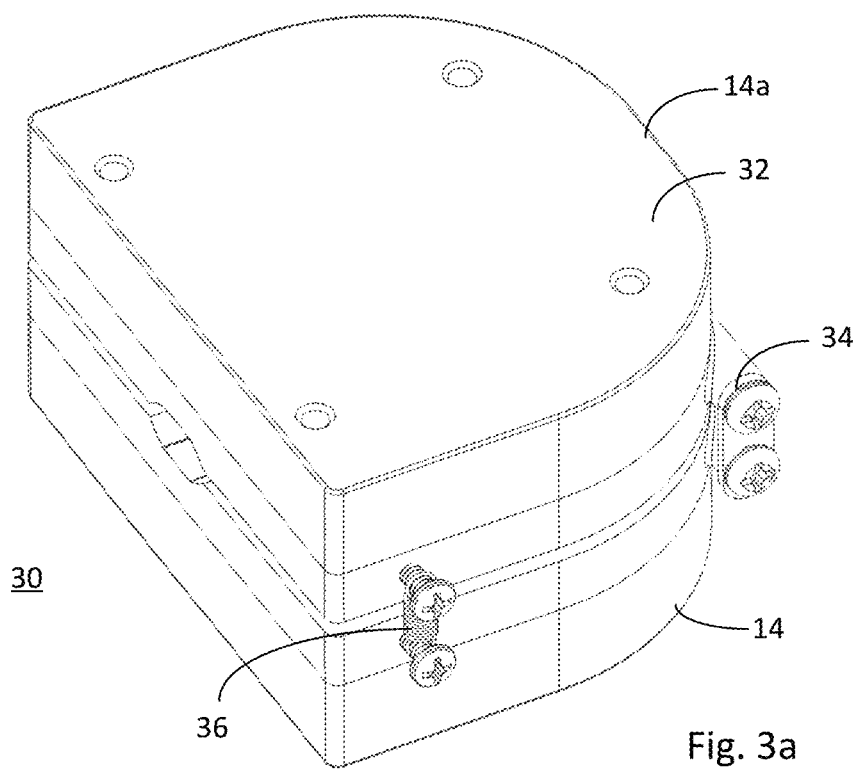
FIG. 3a is an illustration of a combination of LED complexes for use in a multi-channel measurement device according to another aspect of the present invention.
Figure 3B:
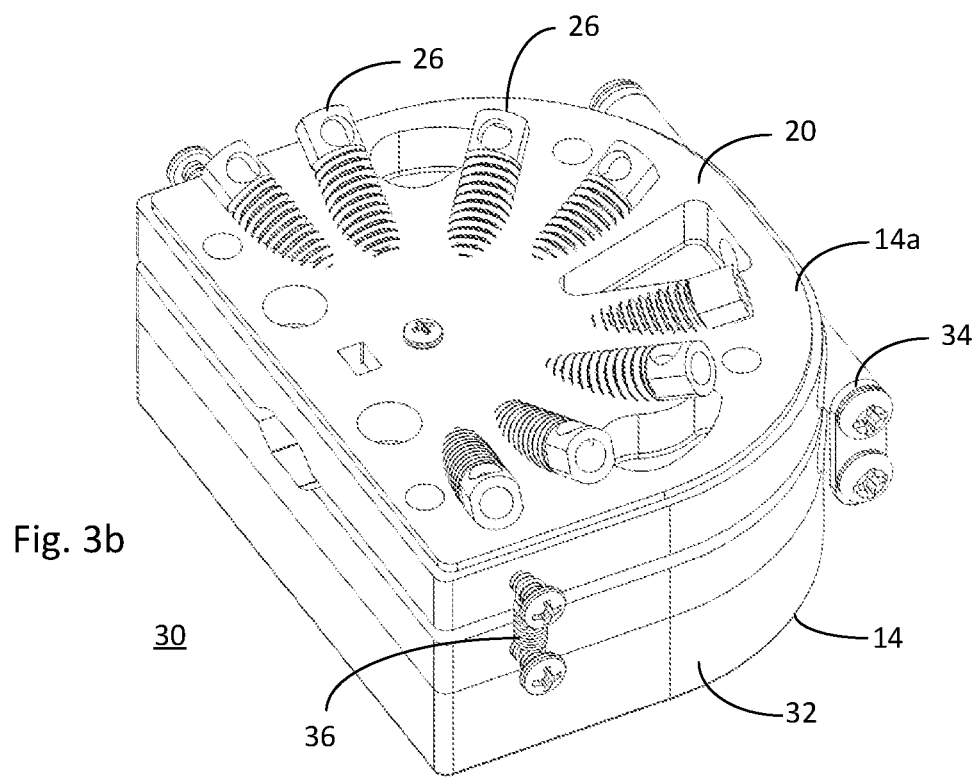
Figure 3C:
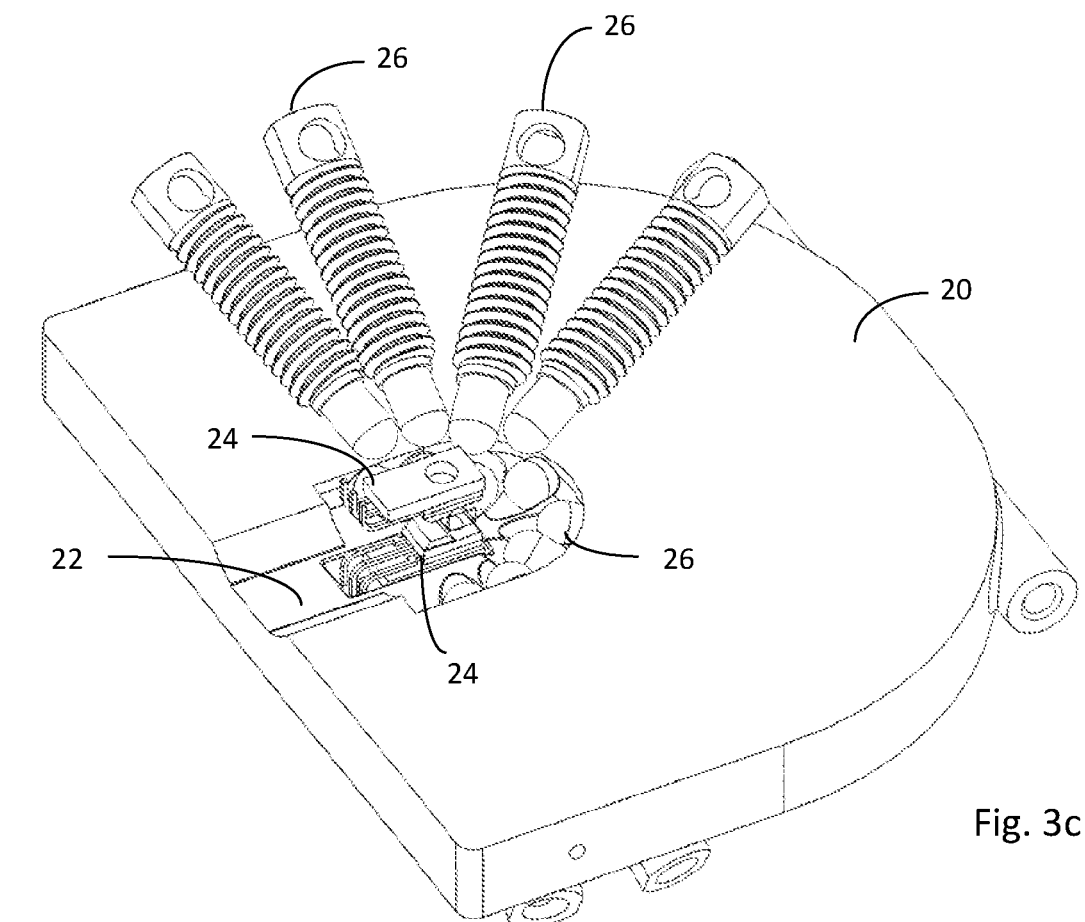

Referring to FIGS. 3a, 3b, and 3c, an example of combining a plurality of Source/Sensor complexes 14a into a Source/Sensor Complex System 30 is provided. Where components are the same or similar between the examples in FIGS. 2a, 2b and FIGS. 3a, 3b and 3c, the same reference characters are used and detailed descriptions of such components are not repeated. Source/Sensor Complex System 30 includes two Source/Sensor Complexes 14a. FIG. 3b illustrates the Source/Sensor Complex System 30 of FIG. 3a with a cover 32 of a Source/Sensor Complex 14a removed to reveal additional detail. FIG. 3c illustrates the Source/Sensor Complex System 30 with additional components of one of the Source/Sensor Complexes 14a removed to reveal additional detail.

Each Source/Sensor Complex 14a includes a housing 20, a finger cavity 22, a sensor 24, and a plurality of sources 26. In the example of FIGS. 3a, 3b, and 3c, eight sources 26 are provided, each corresponding to a distinct measurement band. The Source/Sensor Complex 14a further includes a cover 32. The Source/Sensor Complex System 30 further includes a hinge 34 and springs 36. The hinge 34 and springs 36 cooperate to enclose a patient's finger inside the finger cavities 22 and apply the sensors 24 and sources 26 to the skin of the finger. The hinge 34 and springs 36 are exemplary, and any other suitable means may be employed to provide the function of allowing the Source/Sensor Complexes 14a to separate to admit a finger in the finger cavity, and then compress the sources 26 and sensors 24 on the finger, such as elastomeric materials. Also, in addition to the finger cavity 22, the measurement portion of the device may vary in size and shape depending on the body part and/or tissue to be measured. A Source/Sensor Complex System 30 may also include an additional source/sensor pair recording data with just one source which is not in conjunction with the other complexes to be used as reference. For example, one additional LED/TSL237 complex that only records RED LED at medium intensity for reference may be located about one inch behind the other sensors and sources.

Using multiple Source/Sensor complexes 14a in conjunction with each other allows recording measurements form an exponential amount of sources by a single distinct sensor. While the sources 26 on each Source/Sensor complex 14a may be oriented to allow for data capture on their own complex's sensor 24, the sources 26 may also be oriented to allow for data capture on the other complex' sensor 24. In a Source/Sensor Complex System 30 having two Source/Sensor complexes 14a, and sources providing eight measurement band (e.g., eight bands of light wavelengths), there will be two sources for each measurement band, each capable of being measured by two sensors. For example, energy corresponding to a particular measurement band from a first a source 26 of a on a first Source/Sensor Complex 14a may be be detected by a first sensor 24 on the first Source/Sensor Complex 14a and by a second sensor 24 on a second Source/Sensor Complex 14a. Similarly, energy corresponding to a particular measurement band from a second source 26 of a on the second Source/Sensor Complex 14a may be be detected by the first sensor 24 on the first Source/Sensor Complex 14a and by the second sensor 24 on the second Source/Sensor Complex 14a. This provides four data sources which describe the same natural property response for a given measurement band. Because the geometric relationship between each sensor and each source is known, blood information may be accurately captured even absent of a pulse waveform. These four distinct but related responses may advantageously be exploited to build a "known dataset" in which a neural network can otherwise unobservable relationships.

In a Voltage/Galvanometer complex system, we combine two or more Voltage/Galvanometers to allow for many data sources for each impedance. There is one additional Voltage/Galvanometer at a distance far enough away to stop interaction used as reference.

The data recorded by a Source/Sensor Complex System comes directly from each sensor in the system (including one used for reference). This sensor is chosen based on the specific natural property we are looking for and is of the same type as our source output. Each sensor in the complex system feeds data to our microcontroller at the same time. This data is recorded at a specific rate—usually 8 MHz, but can be increased by bit-shifting up to 64 MHz.

In an LED/light sensor Complex System as described with respect to the examples above, the light sensor such as the exemplary TSL237 sensor changes the frequency of an output square wave based on the intensity of light detected by the light sensor. The frequency of this square wave is detected (at a rate of 8 MHz to 64 MHz) and translated into an intensity value. In a two Source/Sensor Complex System 30, data may be continuously recorded for all 3 TSL237 sensors (two diagnostic sensors and one reference sensor) concurrently.

Three of the components of human tissue which absorb certain spectra of light include the tissue itself, venous blood and arterial blood. Light transmission and reflection through arterial blood varies in intensity with the pulse of the subject. By shifting the capture rate from 8 MHz to 64 MHz and adjusting LED intensity, a pulse waveform is almost always detectable for both diagnostic sensors on all 16 LED sources comprising 32 measurements. When a pulse waveform is detected, the peak intensity value and trough intensity value are recorded as separate data points. This leads to 64 data points for a standard 2 LED/TSL237 Complex System.

Figure 4:
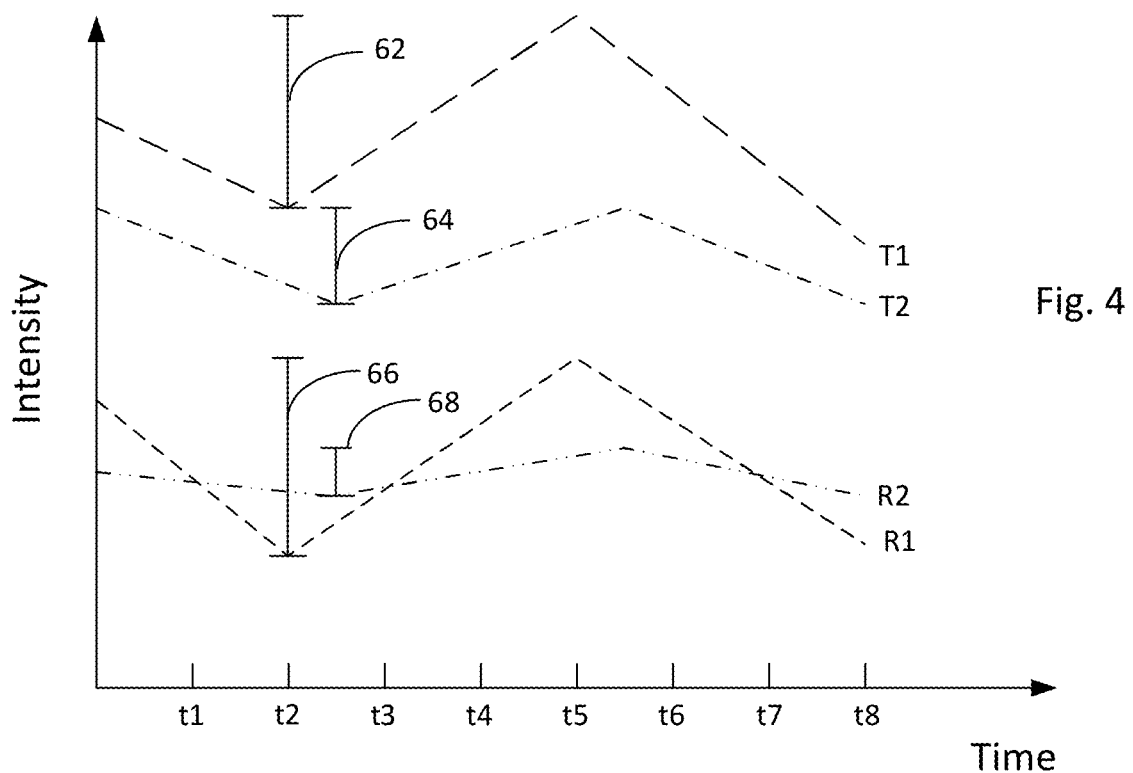
FIG. 4 is an illustration of pulse waveforms for a one measurement band according to another aspect of the present invention.
Figure 5:
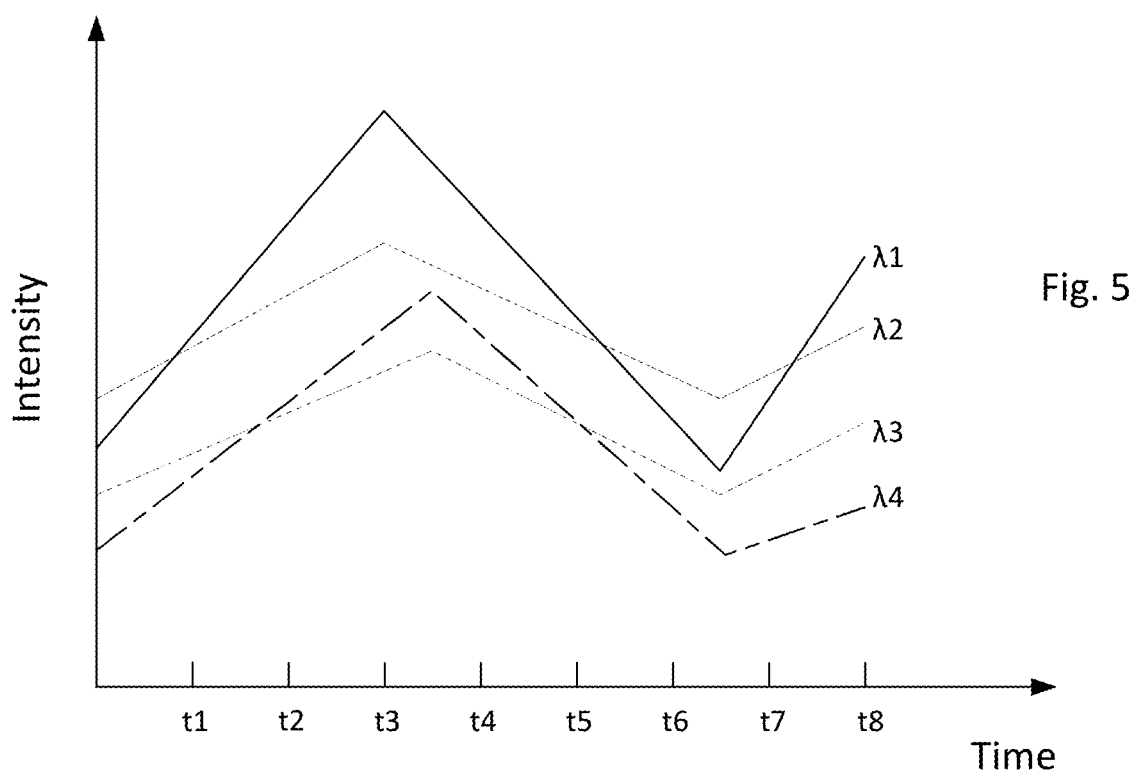
FIG. 5 is an illustration of pulse waveforms at a plurality of different measurement bands according to another aspect of the present invention.

FIGS. 4 and 5 are examples of pulse waveforms. FIG. 4 illustrates for pulse waveforms (T1, T2, R1, R2) for one wavelength. T1 and T2 are pulse waveforms of light intensity transmitted through tissue over time. R1 and R2 are pulse waveforms of light reflected by tissue over time. These correspond to the four measurements discussed above for a particular combination of source 26 and sensor 24 (first Source/Sensor Complex 14a to second Source/Sensor Complex 14a, second Source/Sensor Complex 14a to first Source/Sensor Complex 14a, first Source/Sensor Complex 14a to itself, second Source/Sensor Complex 14a to itself). Measurement bar 62 indicates the peak and trough light intensities of T1 over time internal t2-t5. Measurement bar 64 indicates the peak and trough light intensities of T2 over time internal t2-t5. Measurement bar 66 indicates the peak and trough light intensities of R1 over time internal t2-t5. Measurement bar 68 indicates the peak and trough light intensities of R2 over time internal t2-t5.

FIG. 5 illustrates four pulse waveforms for one sensor 24 sensing four measurement bands 1 λ1, λ2, λ3, λ4 over time. In this example, the measurement bands are bands of wavelengths of light energy. As described above, the sensors 24 and sources 26 may be configured to provide eight or more measurement bands, but only the first four are illustrated in FIG. 5 to improve legibility.

Figure 6:
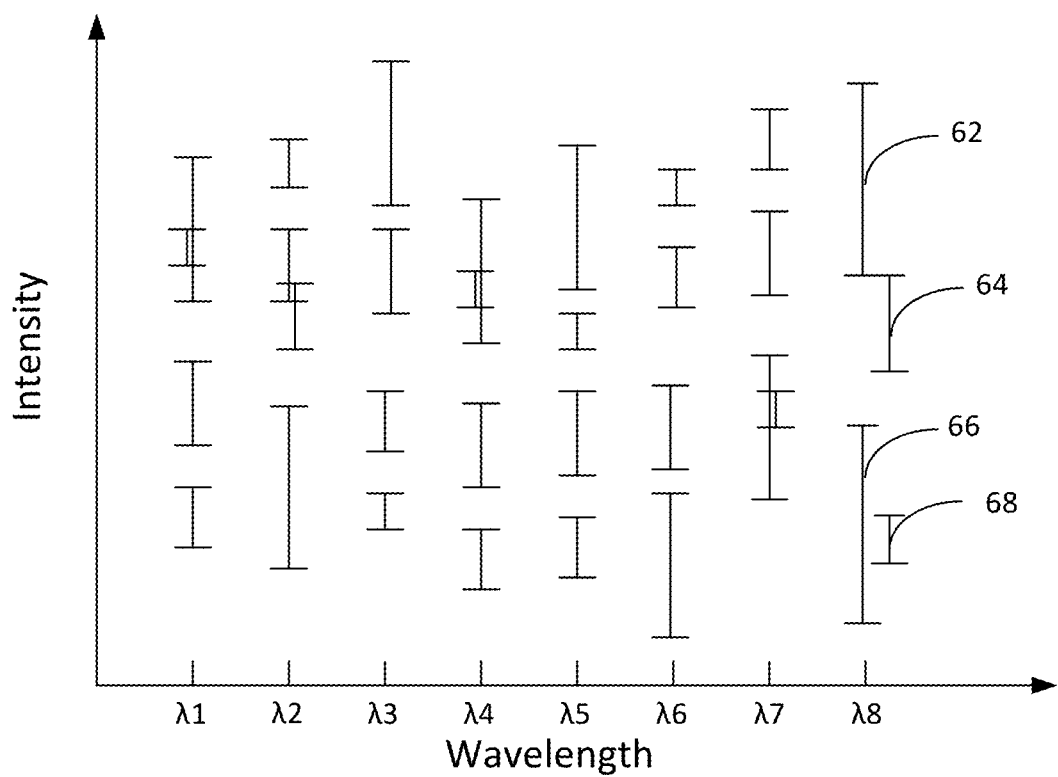
FIG. 6 is a graph of one example of results obtained by a multi-channel measurement device according to the present invention.

FIG. 6 is a depiction of four measurement bars for a given measurement period plotted for eight different measurement bands. Since each measurement band has eight measurement values, 64 points of data are plotted as in FIG. 6.

In the example of a Voltage/Galvanometer Source/Sensor Complex System, the sensor 24 may be a simple dermal conductance electrode and outputs a result of microSiemens (μS). In a two Complex System with three geographically distinct sources, data may be continuously recorded for all three electrodes at the same time. By shifting the capture rate, source impedance, and source voltage, much extra relevant information about the electrochemical properties of this patients blood may be extracted, even if pulse waveforms are not found. This can lead to many data points for a standard 2 Voltage/Galvanometer Complex System.

In order to detect how changes in long-term or short-term blood sugar affect the natural properties of blood, data may advantageously be captured using a Source/Sensor Complex System and associated with results of conventional diagnostic tests on individuals to construct a "known dataset". For example, the natural properties of absorption spectra, electrochemical response, etc. may be recorded with systems as described herein, along with conventional tests/assays for long-term glucose (HbA1C), short-term glucose, beta amyloid, collagen, fibrinogen, cholesterol, etc. A neural network may be trained with the known dataset to detect patterns associated with one or more desired diagnosable medical conditions, even if such patterns would be difficult or impossible to discern by human researchers. Another part of the "known dataset" is used to validate a trained neural network so as to ensure valid results.

Any new measured data from people with unknown clinical properties is then interpreted using the artificial neural network that has undergone supervised training with the known dataset. Any clinical properties for which the neural network has been trained and which have an actual effect on the natural properties for which the Source/Sensor Complex 14, 14a measures will be accurately predicted. This process may be adapted to recording/predicting other clinical properties (e.g. likelihood of cardiac arrest) and/or adapting the Source/Sensor complex to record data relevant to those clinical properties (e.g. galvanic skin response) in order to build lightweight, reusable, point of care diagnostic/screening devices for other diseases. The processes and technologies disclosed herein may also be adapted to wearable devices, to enable constant monitoring of important clinical properties.

A neural network is a computing system that "learns" relationships between input data and output data. It is comprised of series of nodes organized into layers. Each neural network has at least one input layer, one output layer, and zero or more middle/"deep" layers. The nodes between layers are connected to each other. Each node has an associated cost function and weight which describes how it interacts with the nodes it's connected to.

The number of and datatype of each input neuron must correspond to the number of and datatype of our input data. The number of and datatype of each output neuron must correspond to the number or and datatype of our output data. Each neuron weight is usually associated a random, average, or otherwise known value.

Figure 8A:
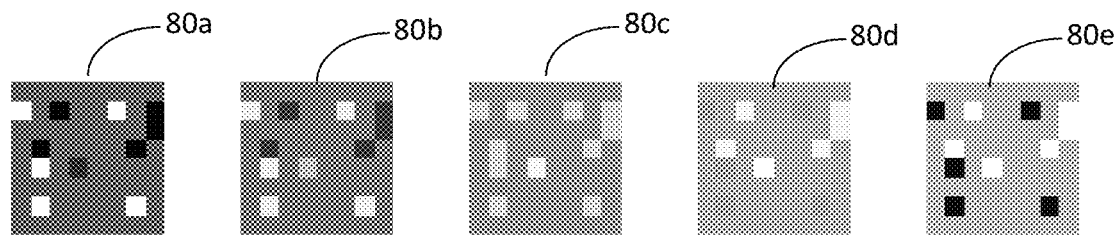
FIG. 8a provides a visual representation of how changes in HbA1C are reflected as linear changes in pixels representing certain measurement results.
Figure 8B:
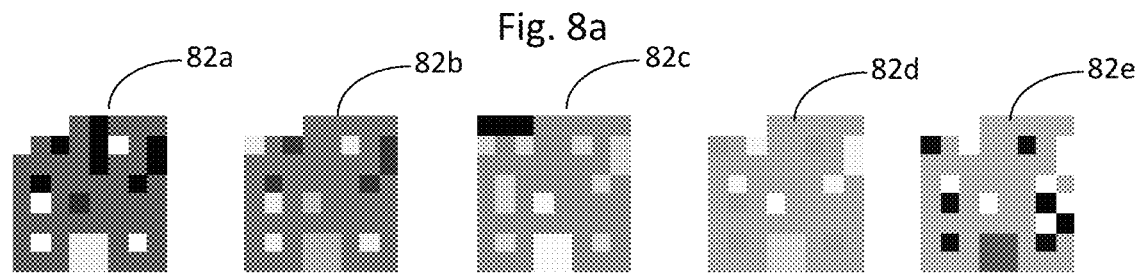
FIG. 8b provides a visual representation of how changes in HbA1C are reflected as non-linear and/or "group" changes in pixels representing certain measurement results.
Figure 8C:
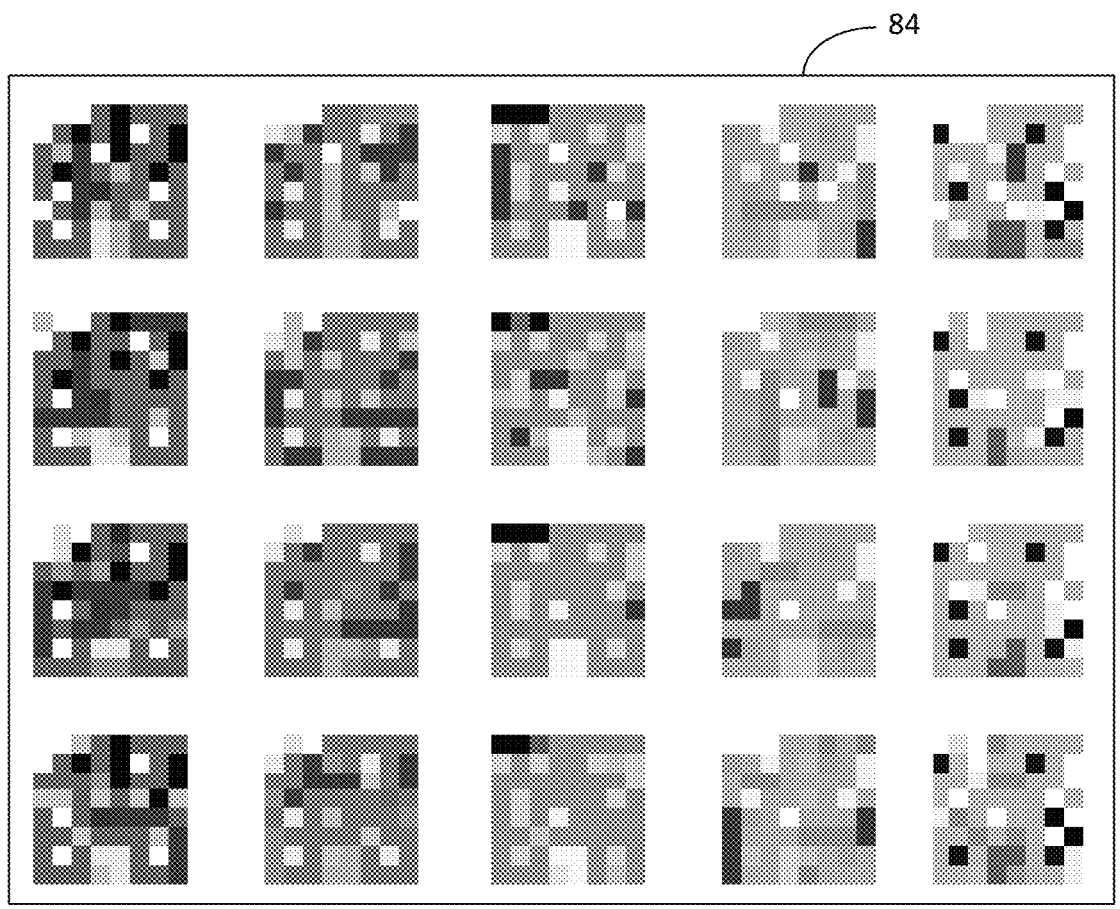
FIG. 8c provides a visual representation of examples of 8×8 grids of pixels of test subjects and their associated HbA1C values.

In the example of the Source/Sensor Complex System 30 described above, 64 data inputs are recorded. These data inputs may be normalized and represented as illustrated in FIGS. 8a, 8b and 8c. In these figures, each of the 64 normalized data inputs recorded by a Source/Sensor Complex System 30 is represented by a pixel in an 8×8 grid. Normalization may involve Feature Scale Normalization: (X−Xmin)/(Xmax−Xmin), Standard Score Normalization: (X−μ)/(std. deviation), or other types of normalization. Dimensionality reduction is also often used to improve results. For example, "least weight analysis" and PCA may be used for dimensionality reduction.

FIG. 8a is a visual representation of how changes in HbA1C are reflected as linear changes of certain points in 8×8 grids 80a, 80b, 80c, 80d and 80e. Some pixels go from low to higher, others go from high to low. The pixels may change at different rates. There may also be "general" changes that affect all pixels. Here, as glycated hemoglobin increases, it may be represented as a general white-value increase for most pixel values as they progress from grid 80a to 80b, but some pixel values reverse from light in grids 80a, 80b and 80c and darken in grids 80d and 80e.

FIG. 8b is a visual representation of how changes in HbA1C are reflected as non-linear and/or "group" changes of sets of pixels in 8×8 grids 82a, 82b, 82c, 82d and 82e. The associated linear changes from FIG. 8a are also depicted. The points do not have to be spatially next to each other. For example, pixels ({4, 1}, {5, 1}, {4, 2}, {5, 2}) ({horiz., vert.} beginning from lower left corner) are generally whiter for HbA1C values under 8.0%, but suddenly flips darker at HbA1C values above or around 8.0%.

FIG. 8c contains additional visual representations 84 of data measured by a measurement device according to the present invention. These are included to show variability in the measured results.

Figure 9A:
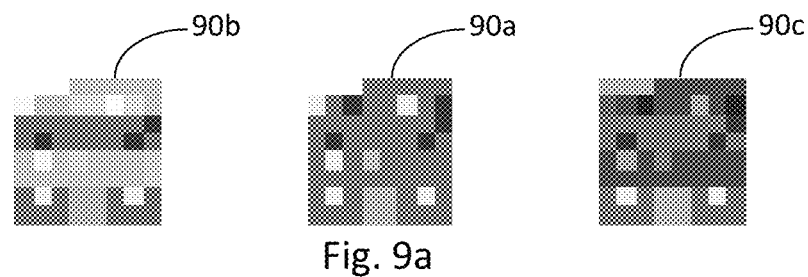
FIG. 9a provides a visual representation of how physical/anatomical changes such as finger size are reflected in the captured data.

FIG. 9a provides a visual representation of how physical/anatomical changes such as finger size are reflected in the captured data. Grid 90a depicts measurements from an average sized finger. Grid 90b depicts measurements from an abnormally small finger. It is characterized by an unchanged reflection AC and DC values, but consistently brighter transmission AC and DC values. Grid 90c depicts measurements from an abnormally large finger. It is characterized by a unchanged reflection AC and DC values, but consistently darker transmission AC and DC values.

Figure 9B:
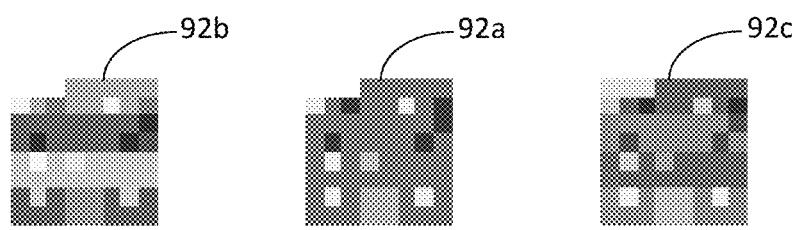
FIG. 9b provides a visual representation of how physical/anatomical changes such as skin color are reflected in the captured data.

FIG. 9b provides a visual representation of how physical/anatomical changes such as skin color are reflected in the captured data. Grid 92a depicts measurements with average skin tone. Grid 92b depicts measurements with abnormally pale/translucent skin. It is characterized by higher transmission AC and DC values, and lower reflection AC and DC values. Grid 92C depicts measurements with abnormally dark skin. It is characterized by lower transmission AC and DC values, and higher reflection AC and DC values.

Figure 9C:
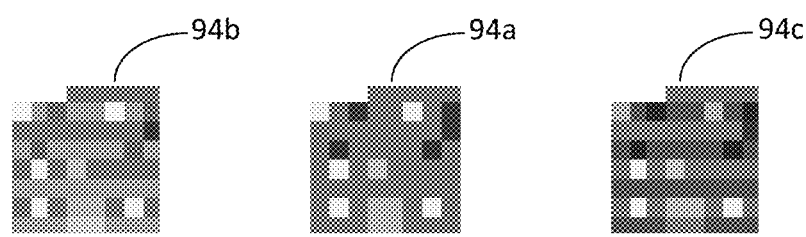
FIG. 9c provides a visual representation of how physical/anatomical changes such as moving vs non-moving blood are reflected in the captured data.

FIG. 9c provides a visual representation of how physical/anatomical changes such as moving vs non-moving blood are reflected in the captured data. Grid 94a depicts measurements of tissue with a normal amount of moving blood. Grid 94b depicts measurements of tissue with an abnormally low amount of moving blood. It is characterized by unchanged DC values, and consistently brighter AC values. Grid 94c depicts measurements of tissue with an abnormally large amount of moving blood. It is characterized by unchanged DC values, and darker brighter AC values.

In a Source/Sensor complex system with [N] complexes, a neural network will have ([#sources]*[#sensors per complex (1)]*[# of points per data source (e.g. AC and DC)]* [N]^2]) input neurons. In the example above, there are 64 data sources in an 8×8 grid. After "least weight analysis", the number of input neurons may be reduced to about 40 to 63 neurons. By performing PCA on these dimensions and/or the dimensions removed from "least weight analysis", the number of neurons may be reduced to the range of 25 to 40 neurons.

The input neurons accept decimal values that correspond to the normalized sensor readings. The output neurons correspond to whatever clinical properties are to be measured and/or predicted. In a "single layer network" the input neurons are connected directly to the output neurons. They may have a linear or more complicated cost function. Error/weight distribution can happen in a feed-forward manner using gradient descent or another algorithm.

In the example of the Source/Sensor Complex System 30 described above, there are 64 inputs, which may be reduced to about 32 neurons after dimensionality reduction. The input neurons accept decimal values that correspond to normalized light sensor values. When trained on long-term glucose levels, the output neuron corresponds to HbA1C. Any other series of clinical properties may also be configured as an output neuron. The neurons may be connected in a single layer or deep network.

In a "deep" network, the input neurons are connected to a series of additional layers. The neurons in the final layer of this additional set of layers are connected to the output neurons. Each neuron in one layer is connected to each neuron in the next layer. In a "deep" network, each neuron may have a linear or more complicated cost function. Error/weight distribution can happen in a feed-forward or back-propagation manner using gradient descent or another algorithm. Techniques like max pooling, dropout neurons, etc. may also be used to improve results in a deep network.

In a Voltage/Galvanometer complex system with 3 complexes, there may be 27 input neurons. If a pulse waveform is detected in the Galvanometer sensor reading, then this may be doubled to 54 input neurons. Dimensionality reduction may be applied in the similar ways. The input neurons accept decimal values that correspond to normalized Galvanometer values. When trained on long-term glucose levels, the output neuron corresponds to HbA1C, but this could be trained on any series of clinical properties.

Once the architecture of a neural network has been constructed, we can train the network with a collection of input data objects and their associated output data objects. For each input data object, we feed the input data through our neural network which predicts output data. We compare this predicted output data to our known output data and distribute the error through our neuron weights in a specific manner (One example of error distribution is gradient descent). By repeating this process for many input and output data objects on the same neural network, the neuron weights will begin to reflect relationships between the input data and output data. The training data set must contain enough input and output data objects in order for the network to pick up on general/population relationships and to reinforce the relationships it detects on individual input/output data objects. Any input/output object used to train the network is "consumed" and cannot be used for predictive analysis.

Figure 7:
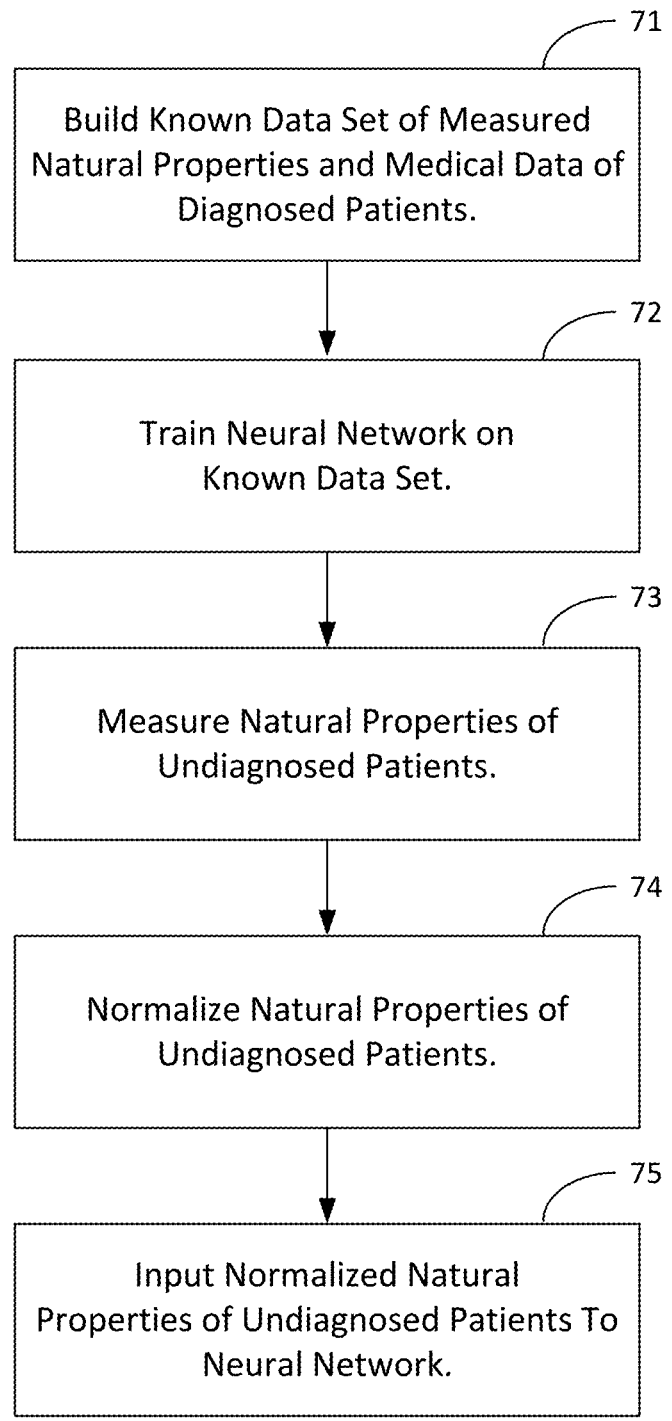
FIG. 7 is a flow chart of a process for training a neural network according to another aspect of the present invention.

FIG. 7 is a flow chart of a process for training a neural network. In order to predict a relevant clinical property based on the data captured from our Source/Sensor Complex System, we must first collect a set of medical records on patients concerning the clinical property to be predicted and then measure the natural properties which are believed to be indicative of the clinical property. In order to collect this data, the Source/Sensor Complex System is applied to a subject. The microcontroller controls which Source is activated, and controls the magnitude/intensity of that source. The microcontroller records the sensor data and records which source is activated and the magnitude of that source. This microcontroller can be controlled by a predefined program, through an online api, or manually by control software on a computer or mobile phone. While continuously recording all sensor data, the control software activates the first source. It may increase or decrease the intensity of this source to allow for optimum data capture (e.g. looking for a pulse waveform or exploring differences in magnitude). It repeats this process for all sources and then all sensor data is saved. This process is repeated on enough patients with measured clinical properties to construct a "known dataset" (step 70). This "known dataset" is used to train our neural network (step 72) which will allow us to predict new information.

Once a neural network has been trained on a "known dataset", the same Source/Sensor Complex System to predict any clinical properties that are present in the "known dataset" and have an underlying relationship to the natural property being measured. The Source/Sensor Complex System is applied to an undiagnosed subject and operated by the microcontroller as described above. The data is recorded in the same way as above, including the natural properties of the subject (step 73). The data is normalized as described above (step 74). The normalized data is either processed and interpreted on-device (using on-device trained neural network) or sent to the web api which processes and interprets the data using the trained neural network (step 75) and returns an answer to the device. This device is then presented to the user or health care professional along with a unique ID. If a clinical property of importance is then measured for this patient, it can be returned to the web api along with the unique ID to further train the neural network. This measured clinical property may or may not be one of the ones predicted by given multiband measurement device 10.

Figure 10:
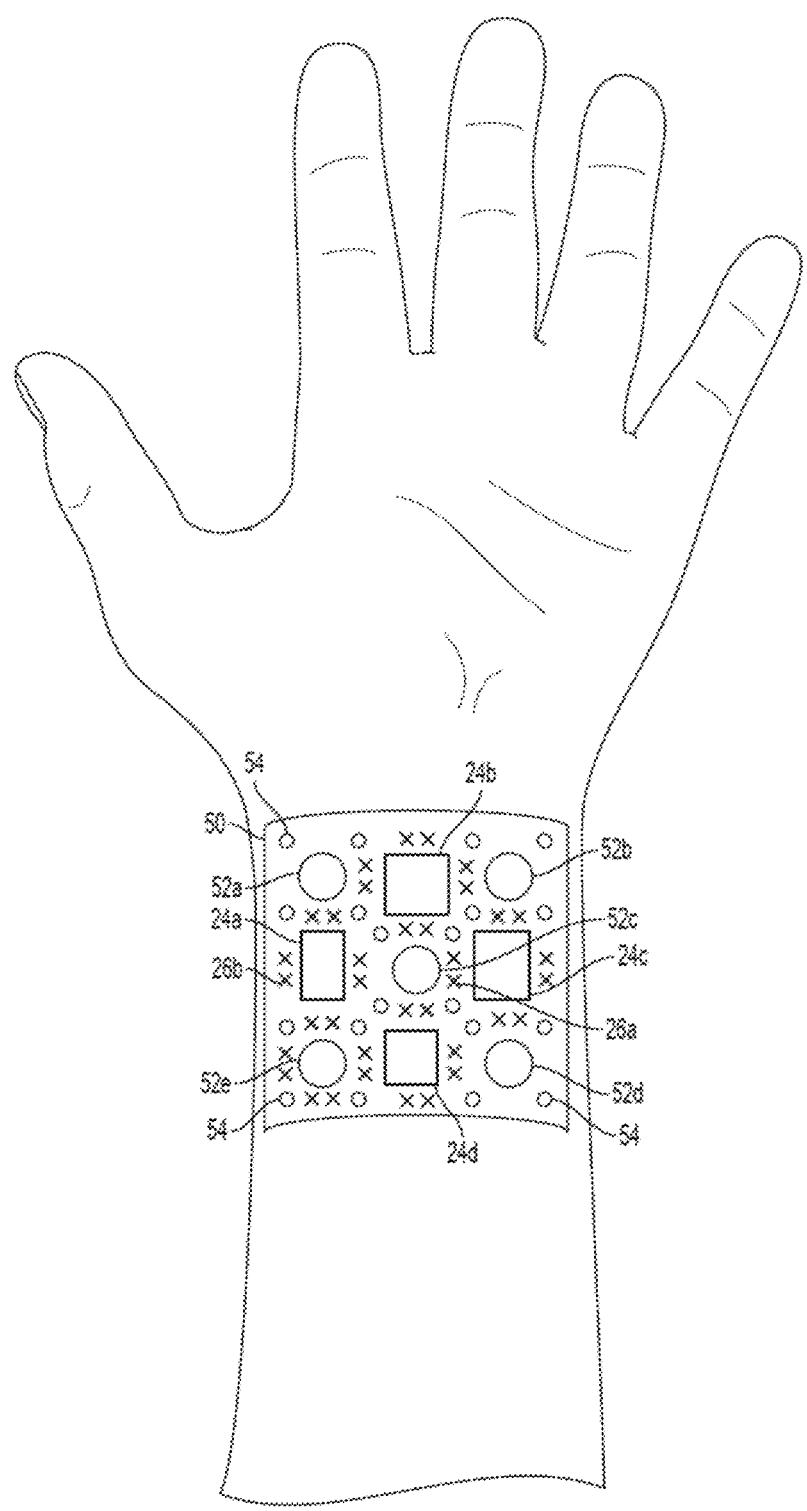
FIG. 10 is an illustration of a wearable multi-channel measurement device according to another aspect of the present invention.

A wearable multi-channel measurement device 50 is illustrated in FIG. 10. In this example, the multi-channel measurement device 50 is wearable on a wrist of a patient. A cover is not illustrated to permit a view of how the sources and sensors are positioned with respect to the skin of a person wearing the device. The multi-channel measurement device 50 includes galvanometers 52a, 52b, 52c, 52d, 52e, and voltage sources 54. The multi-channel measurement device 50 includes light sensors 24a, 24b, 24c 24d, and a plurality of light sources 26a, 26b. Not all of the light sources and voltage sources are labeled for purposes of clarity. The sources/sensors operate as described above, except that the light measurements involve reflective measurements and do not transmit light all the way through the wrist. Multiple sources may provide measurement channels to multiple sensors. For example, light source 26a may be a source for light sensors 24b, 24c and 24d.

The light sources may comprise LED light sources. As described above, there may be five to eight or more different bands of wavelengths of light (both visible and near visible).

Figure 11:
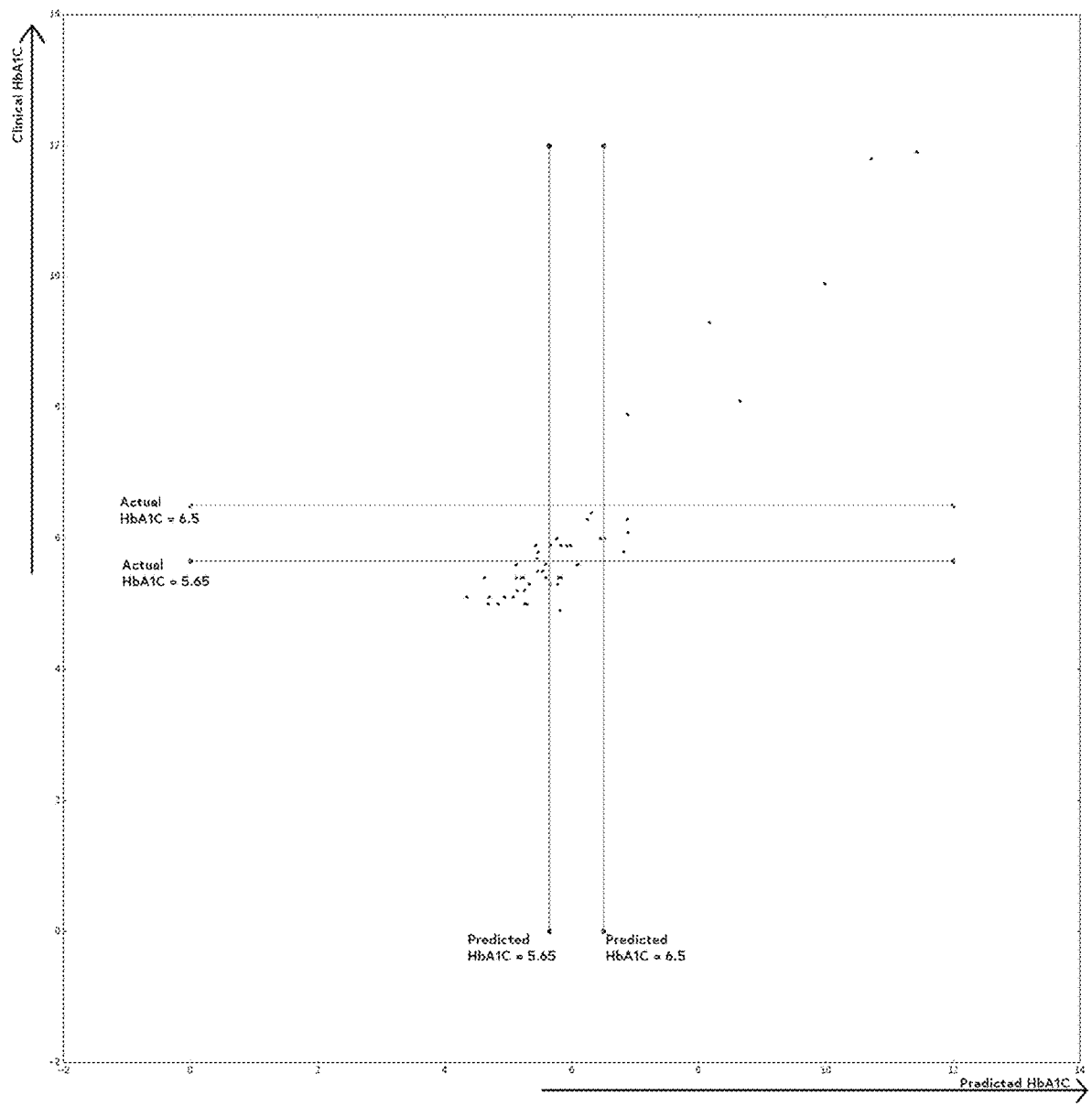
FIG. 11 is a graph comparing HbA1C levels predicted by a device made in accordance with the present invention and HbA1C measured clinically.

FIG. 11 is a graph comparing HbA1C levels predicted by a device made in accordance with the present invention and HbA1C measured by conventional method for 48 patients. The device employed a two Source Complex device with LED light sources and a TSL237 light sensor. The neural network was trained sufficiently to achieve an RA2 predictive value of 0.91 using Leave One Out Cross Validation. Each point on the graph reflects a set of "complete complex system/state data" which was used to predict an HbA1C Value (x coordinate). The Y coordinate is the actual HbA1C value associated with this data. The internal lines on the graph represent threshold values. Left Vertical: Predicted 5.65% (prediabetes) Right Vertical Predicted 6.5% (diabetes); Bottom Horizontal: Actual 5.65% (prediabetes); Top Horizontal: Actual 6.5% (diabetes).

In one example, a multi-channel measurement device for measuring properties of human tissue, may comprise: a housing having a measurement portion adapted to make contact with the tissue; at least one sensor mounted in the housing and exposed through the measurement portion of the housing, the sensor being capable of detecting a measurement energy; a plurality of sources of measurement energy mounted in the housing and exposed through the measurement portion of the housing, the plurality of sources of measurement energy being arranged to at least partially surround the sensor; wherein each combination of one of the sources of measurement energy and sensor provides a different measurement channel.

In the multi-channel measurement device of the above example, the measurement energy may be electrical energy. The sources and sensors may be electrogalvanic, and the sources have impedances different from each other. There may be at least 3 difference impedance values.

In the multi-channel measurement device of the above example, the measurement energy may be light. In the multi-channel measurement device of the above example, the sensor may be a light sensor and each of the plurality of sources of measurement energy is an LED light source.

In the multi-channel measurement device of the above example, the measurement portion of the housing may comprise a finger cavity; the sensor may be a light sensor disposed in the finger cavity; and each of the plurality of sources of measurement energy is an LED light source disposed in the finger cavity and angled to direct light energy toward the light sensor. Each of the LED light sources may produce light at a different wavelength.

What is claimed is:

1. A multi-channel measurement device for measuring properties of human tissue, comprising:
   a microcontroller;
   a first source/sensor complex comprising a first housing having a first measurement portion, a first light sensor coupled to the microcontroller and exposed to the first measurement portion, and a first plurality of light sources coupled to the microcontroller and exposed to the first measurement portion;
   a second source/sensor complex comprising a second housing having a second measurement portion, a second light sensor coupled to the microcontroller and exposed to the second measurement portion, and a second plurality of light sources coupled to the microcontroller and exposed to the second measurement portion;
   the first and second housings of the first and second source/sensor complexes being coupled to each other in an opposing relationship such that the first measurement portion is opposite the second measurement portion and human tissue may be placed between the first and second measurement portions;
   the first plurality of light sources being angled toward the second light sensor such that a portion of the emitted light energy is reflected to the first light sensor and a portion of the emitted light energy is transmitted to the second light sensor by human tissue placed between the first and second measurement portions;
   the second plurality of light sources being angled toward the first light sensor such that a portion of the emitted light energy is reflected to the second light sensor and a portion of the emitted light energy is transmitted to the first light sensor by human tissue placed between the first and second measurement portions;
   the microcontroller being configured with instructions stored in non-volatile memory that, when executed by the microcontroller, cause the microcontroller to individually activate each of the light sources of the first and second pluralities of light sources and to record light intensity detected by the first and second light sensors while an individual light source is activated;
   wherein each combination of an individually activated light source and one of the first and second light sensors provides a distinct measurement channel for measuring the absorption spectra of human blood and tissue.

2. The multi-channel measurement device of claim 1, wherein the first plurality of light sources produces light at a plurality of different wavelengths including red, blue and green wavelengths; and wherein the second plurality of light sources produces light at a plurality of different wavelengths including red, blue and green wavelengths.

3. The multi-channel measurement device of claim 1, wherein the first plurality of light sources comprises at least five LED light sources configured to emit light at wavelengths different from each other; and wherein the second plurality of light sources comprises at least five LED light sources configured to emit light at wavelengths different from each other.

4. The multi-channel measurement device of claim 1, wherein the first plurality of light sources comprises eight LED light sources configured to emit light at wavelengths different from each other; and wherein the second plurality of light sources comprises eight LED light sources configured to emit light at wavelengths different from each other.

5. The multi-channel measurement device of claim 1, wherein the first measurement portion comprises a first finger cavity and the second measurement portion comprises a second finger cavity.

6. The multi-channel measurement device of claim 1, wherein the instructions stored in non-volatile memory further comprise instructions which, when executed by the microcontroller, cause the microcontroller to provide signals to adjust a light intensity emitted by an individually activated light source based on a light intensity detected by the first and second light sensors.

7. The multi-channel measurement device of claim 1, wherein the first and second light sensors comprise light to frequency converters.

8. The multi-channel measurement device of claim 1, wherein the first and second light sensors are recessed in their respective housings to reduce detection of interfering light.

9. The multi-channel measurement device of claim 1, further comprising a light barrier around each of the first and second light sensors to reduce detection of ambient light.

10. The multi-channel measurement device of claim 1, further comprising an additional light source and light sensor combination for use as an external reference point.

11. The multi-channel measurement device of claim 1, further comprising a processor coupled to the microcontroller and configured with instructions stored in non-volatile memory which, when executed, cause the processor to:
signal the microcontroller to begin a measurement cycle;
receive measurement data obtained by the microcontroller;
process the measurement data to obtain a clinical result.

12. The multi-channel measurement device of claim 11 further comprising a trained neural network, wherein processing the measurement data to obtain a clinical result comprises inputting the measurement data to the neural network.

13. A system for measuring properties of human tissue and returning a clinical result, comprising:
a neural network trained on a known data set having multiple measurement channel data corresponding to an absorption spectra of human blood and tissue to identify a clinical result from the data;
a multi-channel measurement device as recited in claim 1 and further comprising a communications interface, the multi-channel measurement device further being configured to transmit measurement data to the neural network;
a user interface configured to receive a clinical result identified by the neural network and display it to a user.

14. The system of claim 13, wherein the user interface is located on the multi-channel measurement device.

15. The system of claim 13, wherein the neural network is located on a server remote from the multi-channel measurement device.

16. The system of claim 13, wherein the neural network is located on a server remote from the multi-channel measurement device and the user interface is on a mobile device.

17. The system of claim 13, wherein the neural network and the user interface are located on a mobile device.

18. The multi-channel measurement device of claim 1, wherein the instructions stored in non-volatile memory further include instructions which, when executed, cause the microcontroller to record data from the first and second sensors concurrently.

* * * * *